United States Patent [19]
Schiek, Sr.

[11] Patent Number: 5,316,022
[45] Date of Patent: May 31, 1994

[54] SPORTS BELT WITH CINCHABLE FASTENER SYSTEM

[76] Inventor: James W. Schiek, Sr., 1020 Winnebago St., Oshkosh, Wis. 54901

[21] Appl. No.: 937,937

[22] Filed: Aug. 28, 1992

[51] Int. Cl.⁵ .......................... A61F 5/37; A61F 5/00; A41F 3/02
[52] U.S. Cl. ..................................... 128/876; 602/19; 2/338
[58] Field of Search ............ 2/338, 336, 311, DIG. 6; 602/19; 128/876, DIG. 15, 875

[56] References Cited

U.S. PATENT DOCUMENTS

| | | | |
|---|---|---|---|
| 3,400,710 | 9/1968 | Goldstein | 602/19 |
| 4,528,700 | 7/1985 | Johnston | 2/338 |
| 4,576,154 | 3/1986 | Hyman | 602/19 |
| 4,907,576 | 3/1990 | Curlee | 602/19 |
| 4,964,401 | 10/1990 | Taigen | 602/19 |
| 4,991,573 | 2/1991 | Miller | 602/19 |
| 5,070,866 | 12/1991 | Alexander | 602/19 |
| 5,086,758 | 2/1992 | Schiek | 2/338 |
| 5,147,261 | 9/1992 | Smith | 602/19 |

Primary Examiner—Michael A. Brown
Attorney, Agent, or Firm—Robert C. Curfiss

[57] ABSTRACT

A one-way hook and loop fastener system is incorporated on a cinchable belt for providing a cinchable fastener which may be tightened in one direction without disengaging the fastener elements from one another. The natural tension on the belt when tightened engages and locks the fasteners in the opposite direction.

7 Claims, 1 Drawing Sheet

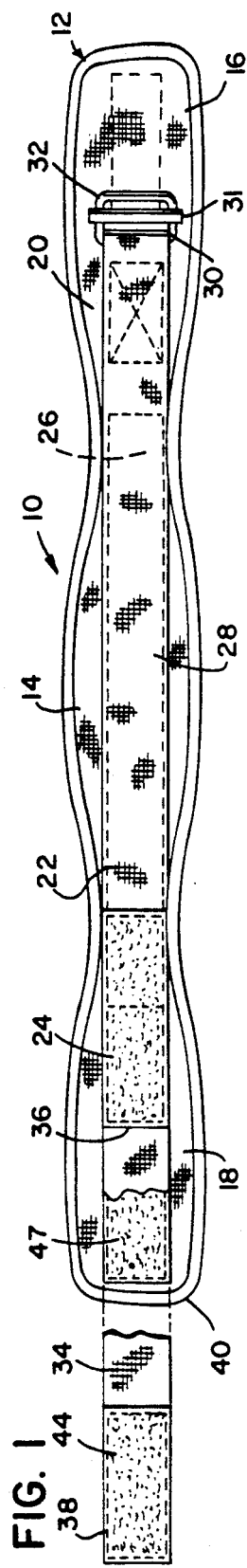
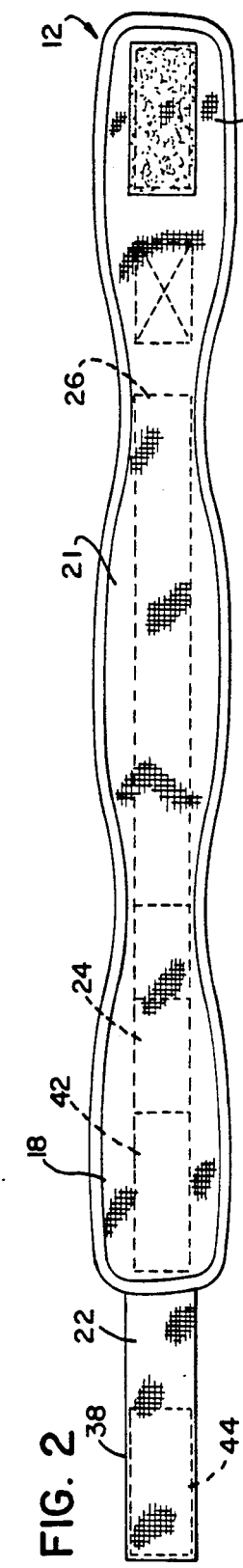
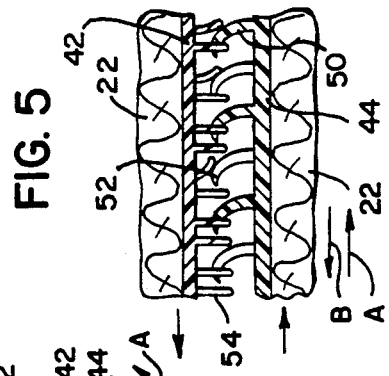
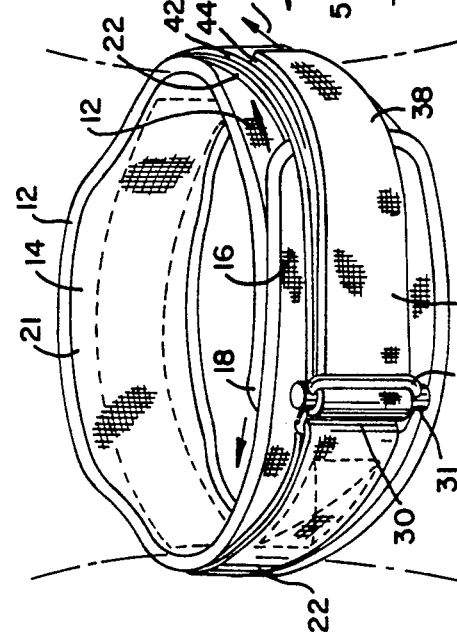
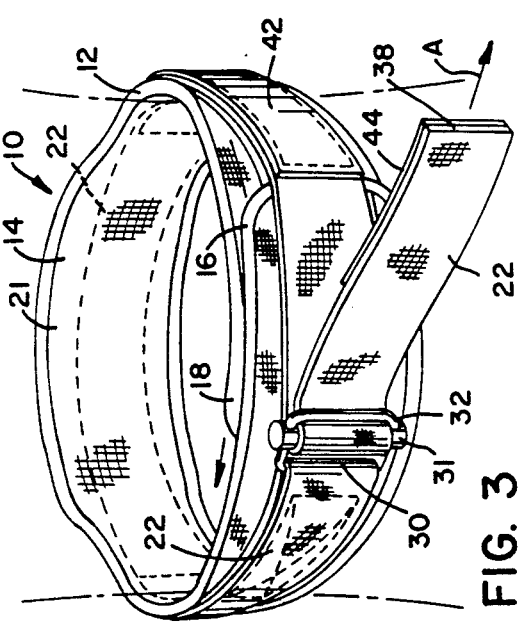

SPORTS BELT WITH CINCHABLE FASTENER SYSTEM

BACKGROUND OF THE INVENTION

1. Field of the Invention

The invention is generally related to sports belts such as, by way of example, weight lifting belts and the like, and is specifically directed to a sport belt having a cinchable one way hook and loop type fastener system.

2. Description of the Prior Art

Sports belts such as weightlifting belts and the like are well known. Typically, the belt includes a support pad for supporting the lower lumbar region of the back, an abdominal pad for providing support on the abdominal wall of the wearer, and a fastener system which allows the belt to be securely tightened around the waist of the wearer.

It is common to provide cinchable fasteners on such belts. A dual fastener system is often used, wherein the belt is placed around the waist of the user and held in position by a first fastener system. The belt is then cinched and tightened by a second fastener system to provide a snug, supporting fit.

Examples of such belts are shown in my earlier patents and co-pending applications, as follows:

- U.S. Pat. No. 5,086,488, entitled: Support Device, dated Sep. 9, 1991;
- U.S. Pat. No. 5,086,758, entitled: Belt Support Device With Adjustable Hook & Loop-Type Fastener, dated Feb. 11, 1992;
- U.S. application Ser. No. 07/728,742, entitled: Support and Utility Belt, filed Jul. 12, 1991, Amendment filed Jul. 21, 1992; and
- U.S. application Ser. No. 07/665,980, entitled: Adjustable Hook and Loop-Type Fastener Assembly, filed Mar. 7, 1992, Final Fee Paid Jul. 23, 1992.

Over the years it has become desirable to use hook and loop type fastener systems because of the ease and efficiency of their application. Also, such fasteners are infinitely adjustable, permitting the belt to be used on a variety of users with maximum comfort and fit, providing a great advantage over loop and tongue type fastener systems which are only incrementally adjustable.

One of the problems with hook and loop type fasteners is their tendency to become semi-permanently secured upon contact, making them undesirable for use in cinchable type fastener systems. One way of solving this problem is shown in my earlier U.S. application Ser. No. 07/665,980. As there shown, a removable flap is positioned over the pad on one of the fastener elements, precluding contact between the fastener elements until the belt is properly cinched about the waist. This permits the hook and loop type fastener system to be utilized on a cinchable fastener design.

There remains, however, a need for a hook and loop type fastener which is cinchable in one direction and semipermanently secured in the opposite direction, greatly enhancing the use of hook and loop type fastener elements in cinchable securing systems.

SUMMARY OF THE INVENTION

The sport belt of the subject invention includes a oneway hook and loop type fastener for a cinchable fastener system for providing the mechanism for cinching a belt around the waist of the user to provide maximum comfort and fit. When the belt is placed about the waist of the wearer the oneway fastener is used to cinch or tighten the belt. This provides variable comfort and fit for a variety of users utilizing a belt of a single length.

In the preferred embodiment, the hook and loop type fastener system includes a standard loop patch on one of the fastening elements. However, unlike in past hook and loop type fastener systems, the hook element has hooks which are all biased in the same direction. This permits the hooks to slide through the loop section without engaging any of the loops when the fasteners are moved in one direction relative to the other, but permits the hooks to engage the loops when the fastener elements are moved in the opposite direction relative to one another.

This fastener system is ideally suited for a cinchable fasteners on sports belts and the like, wherein the wearer places the belt around his waist and then places the fastener elements in juxtaposition with one another as he cinches the belt to the proper fit. By sliding the fastener systems in the cinching direction, and having the hooks biased in the opposite direction, the hook and loop fastener patches do not engage one another but are permitted to slide freely. Once the belt is properly fit about the waist of the user, the fasteners are positioned in engagement with one another and the natural force on the belt due to the tightness around the waist of the user causes the fastener patches to be urged in the opposite direction relative to one another.

By biasing the hooks in this direction, the hook and loop type fastener system is engaged and permanently secured in the same manner as prior hook and loop fasteners. This allows the wearer to place a belt around his body, holding in place the main strap and tightening it, permitting the hook and loop type fasteners to slide into position. When released, they are properly secured by the back tension provided by the natural tension on the belt as it is tightened around the waist.

It is, therefore, an object and feature of the invention to provide a sport belt having a cinchable fastener element utilizing hook and loop type fastener elements.

It is a further object and feature of the subject invention to provide a cinchable sport belt having a hook and loop type fastener system wherein the hook and loop fastener elements are slidable in a first direction and are engageable in a locking relationship in the opposite direction.

It is a further object and feature of the invention to provide a cinchable sport belt having a hook and loop type fastener system wherein the hook and loop type fastener elements are movable to cinch the belt about the waist of the user without use of a protective pad on the hook and loop fastener elements.

Other objects and features of the invention will be readily apparent from the accompanying drawing and descriptions.

BRIEF DESCRIPTION OF THE DRAWINGS

FIG. 1 is a front elevation view of a sport belt including the one way hook and loop type fastener system of the subject invention.

FIG. 2 is a rear elevation of the belt in FIG. 1.

FIG. 3 is an illustration of the belt of FIGS. 1 and 2, encircling the waist of a user and prior to cinching the belt in position.

FIG. 4 is a view similar to FIG. 3, showing the belt in the cinched position.

FIG. 5 is an enlarged sectional view showing a crossection of the one-way fastener system utilized in the belt of FIGS. 1–4.

DETAILED DESCRIPTION OF THE PREFERRED EMBODIMENT

A sport belt 10 in accordance with the subject invention includes a primary support structure 12 made of a flexible, non-stretchable material and including an enlarged back support pad 14 at the center of the structure 12 and outer abdominal support members 16 and 18. On the outer surface 20 of the belt structure 12 is an elongated strap 22 secured to the surface 20 at areas 24 and 26. In the preferred embodiment the strap is also secured to the abdominal pad area 14 as shown at 28. The belt may be secured to the structure 12 in any number of desired methods and is shown as stitched directly to the outer surface 20 of the structure 12 in the preferred embodiment.

The outer end 30 of the belt 22 is looped for holding a slide buckle 32 which is disposed directly over the abdominal pad 16. The outer end 34 of the belt is free outwardly of the stitch line 36 and has an extension 38 which extends beyond the outer edge 40 of the base structure 12. The base structure includes a hook and loop type fastener patch 42 which is in overlying relationship with the abdominal pad 18 and a complementary hook and loop type fastener patch 44 adjacent the outer end 38 of the strap 22.

As show in FIGS. 3 and 4, the belt 10 is adapted to be encircled about the waist of a user with the inside surface 21 (see FIG. 2) positioned against the body of the wearer. The abdominal pad 14 is positioned against the lower lumbar area of the back for providing firm support during exercise activities. The first abdominal pad 18 is positioned against the abdominal wall of the wearer and the second abdominal pad 16 is positioned directly over the first abdominal pad, as shown in FIG. 3. The outer end 38 of the strap 22 is then inserted through the slide buckle 30 and then up over and back under the bar 31 for securing the belt in the slide buckle in the normal fashion. The outer end 38 of the strap is then grasped by the user's hand and pulled in the direction of the arrow A (FIG. 3), for cinching the belt about the waist of the wearer by tightening the belt to the desired fit. The slide buckle 30 then holds the belt in position and the fastener patches 44 and 42 may be engaged to lock the belt in position.

In use, it is usually desirable to recinch the belt from time to time during use or to adjust the belt after it has been initially cinched in order to increase the comfort level of the user. Typically, the belt is retightened several times during a fitting and often again during a workout. In the past, it was necessary to completely remove the contacting fastener patches 42 and 44 from engagement with one another in order to cinch the belt. In the preferred embodiment of the invention, and as particularly shown in FIG. 5, the one-way hook and loop type fastener pads may be utilized to permit cinching of the belt, even after it is in the tightened position shown in FIG. 4 and without first removing the fastener patch 44 from engagement with the fastener patch 42. Specifically, the belt may be moved in the direction of arrow A while the fastener patches are in contact with one another but will not move in the opposite direction as long as the fastener patches stay in contact, providing a cinching, fastening system.

With specific reference to FIG. 5, it will be noted that the fastener patch 44 includes a plurality of hooks 50 each of which has an upper tip 52 biased toward the left (as drawn). The fastener patch 42 includes a plurality of loops 54 each adapted to engage the tip 52 of the hooks 50. As can be clearly seen from FIG. 5, when the patch 44 is moved in the direction of arrow A relative to patch 42, the tips 52 will slide under the loops 54, permitting the belt to be cinched in the direction of arrow A. As soon as the belt fastener is released by the hand of the user, the natural tension on the belt will pull the fastener patch 44 in the direction of arrow B, urging the tips 52 of the hooks 50 into the loops 54 for securing the belt in position. The one-way hook and loop type fastener system of the subject invention provides a cinchable hook and loop type fastener for a cinchable belt, wherein the belt can be cinched without disengaging the fastener components from one another.

While certain features of the invention have been described in detail herein, it will be understood that the invention encompasses all modifications and enhancements within the scope and spirit of the following claims.

What is claimed is:

1. A belt with a cinching fastener, the fastener comprising:
   a. a first fastening element having a plurality of projecting, closed loops;
   b. a second fastening element having a plurality of projecting hooks all of which include outer tips biased in a common direction and adapted to engage the loops of the first fastening element when moved relative to the loops in a first direction and to slide freely relative to the loops when moved in a second, opposite direction, whereby the hooks of the second fastening element and the loops of the first fastening element become locked in engagement when the second fastening element is pressed against the first fastening element and the fastening elements are moved relative to one another in the first direction causing the hooks to enter into the loops and secure the belt in a position; and whereby the hooks of the second fastening elements and the loops of the first fastening element do not become engaged but slide freely relative to each other when the first fastening element and the second fastening element are moved relative to one another in the second opposite direction.

2. The belt of claim 1, wherein the fastener further comprises:
   a. a base for supporting the first fastener element; and
   b. a strap having opposite free ends and secured to the base, the second fastening element being secured to the strap adjacent one free end thereof.

3. The belt of claim 2, wherein the fastener further comprises a buckle secured to the other free end of the strap and adapted for receiving the one free end thereof.

4. The belt of claim 1, wherein the belt further includes an elongated support structure formed of a flexible, non-stretchable material and including opposite outer ends and a mid-section therebetween, the mid-section adapted to be placed against the back of a user and the outer ends adapted to be wrapped around the waist of the user and placed in overlying relationship with one another over the abdomen of the user, wherein the fastener is adapted to secure the belt but also allows the outer ends to be cinched tightly around the waist of the user.

5. The belt of claim 4, wherein the first fastener element is secured relative to the support structure, and wherein there is further included a strap having opposite free ends and secured to the support structure, the second fastening element being secured to the strap adjacent one free end thereof.

6. The belt of claim 5, wherein the fastener further comprises a buckle secure to the other free end of the strap and adapted for receiving the one free end thereof.

7. The belt of claim 5, wherein the strap is stitched to the mid-section of the support structure.

* * * * *